United States Patent
Morrell et al.

(10) Patent No.: US 9,885,603 B2
(45) Date of Patent: Feb. 6, 2018

(54) RADIATED LIGHT FILTERING FOR A FLOW CYTOMETER

(71) Applicant: BECKMAN COULTER, INC., Brea, CA (US)

(72) Inventors: Michael M. Morrell, Wellington, CO (US); Timothy Reed, Boulder, CO (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/776,878

(22) PCT Filed: Mar. 14, 2014

(86) PCT No.: PCT/US2014/029058
§ 371 (c)(1),
(2) Date: Sep. 15, 2015

(87) PCT Pub. No.: WO2014/144585
PCT Pub. Date: Sep. 18, 2014

(65) Prior Publication Data
US 2016/0025557 A1  Jan. 28, 2016

Related U.S. Application Data

(60) Provisional application No. 61/798,548, filed on Mar. 15, 2013.

(51) Int. Cl.
*G01J 1/04* (2006.01)
*G01N 21/85* (2006.01)
(Continued)

(52) U.S. Cl.
CPC ........ *G01J 1/0488* (2013.01); *G01N 15/1434* (2013.01); *G01N 15/1459* (2013.01);
(Continued)

(58) Field of Classification Search
CPC ..... G01J 1/0488; G01N 21/53; G01N 21/532; G01N 21/6452; G01N 21/85; G01N 15/1459; G01N 15/1484; G01N 15/1486
See application file for complete search history.

(56) References Cited

U.S. PATENT DOCUMENTS 4,178,103 A    11/1979  Wallace
5,090,808 A     2/1992  Ishikawa et al.
(Continued)

FOREIGN PATENT DOCUMENTS

WO    WO 2014/151049    9/2014

OTHER PUBLICATIONS

International Search Report for International Application No. PCT/US2014/029058 dated Jun. 27, 2014 (3 pages).
(Continued)

*Primary Examiner* — Sang Nguyen
(74) *Attorney, Agent, or Firm* — Merchant & Gould P.C.

(57) ABSTRACT

A filter mask for use in a flow cytometer includes light blocking features and light passing apertures. The flow cytometer operates to evaluate one or more characteristics of a sample by illuminating the sample and a carrier fluid and collecting light rays that are radiated from the sample and the carrier fluid. The light rays are passed through the filter mask. The light blocking features of the filter mask are arranged to selectively block radiated light at certain radiation angles, while permit light rays having other radiation angles to pass therethrough. A sensor analyzer receives the light rays that pass through to evaluate at least one characteristic of the sample. The light rays can also be separated into two beams, which can be independently filtered using different filter masks. The results can then be compared to provide even more information regarding characteristics of the sample.

25 Claims, 14 Drawing Sheets

(51) Int. Cl.
  *G01N 21/53* (2006.01)
  *G01N 15/14* (2006.01)
  *G01N 21/59* (2006.01)
  *G01N 15/10* (2006.01)

(52) U.S. Cl.
  CPC ............. *G01N 21/53* (2013.01); *G01N 21/59* (2013.01); *G01N 21/85* (2013.01); *G01N 2015/1006* (2013.01)

(56) References Cited

U.S. PATENT DOCUMENTS

| | | |
|---|---|---|
| 5,125,737 A | 6/1992 | Rodriguez et al. |
| 5,540,494 A | 7/1996 | Purvis, Jr. et al. |
| 5,798,827 A | 8/1998 | Frank et al. |
| 6,404,493 B1 | 6/2002 | Altendorf |
| 6,784,981 B1 | 8/2004 | Roche et al. |
| 7,324,194 B2 | 1/2008 | Roche et al. |
| 7,385,682 B2 | 6/2008 | Chu et al. |
| 7,561,267 B2 | 7/2009 | Luo et al. |
| 8,094,299 B2 | 1/2012 | Wells et al. |
| 2004/0189971 A1 | 9/2004 | Nagai et al. |
| 2004/0189977 A1 | 9/2004 | Nagai et al. |
| 2005/0051706 A1* | 3/2005 | Witney ............... G01N 21/6452 250/214 R |
| 2005/0190376 A1* | 9/2005 | Wegmann ............... G03F 7/706 356/509 |
| 2008/0024758 A1 | 1/2008 | Tabata |
| 2011/0157692 A1 | 6/2011 | Lin et al. |
| 2013/0016335 A1* | 1/2013 | Lo ........................... G01P 5/001 356/28 |

OTHER PUBLICATIONS

International Written Opinion for International Application No. PCT/US2014/029058 dated Jun. 27, 2014 (5 pages).

* cited by examiner

RADIATED LIGHT FILTERING FOR A FLOW CYTOMETER

CROSS REFERENCE TO RELATED APPLICATION(S)

This application is a National Stage of PCT International Patent application No. PCT/US2014/029058, filed 14 Mar. 2014, which claims benefit of U.S. Ser. No. 61/798,548, filed on 15 Mar. 2013, titled RADIATED LIGHT FILTERING FOR A FLOW CYTOMETER and which applications are incorporated herein by reference in their entireties. To the extent appropriate, a claim of priority is made to each of the above disclosed applications.

BACKGROUND

Flow cytometers are used to evaluate the content of a sample. The sample is introduced into a fluid stream, which is then illuminated with a light beam. When the light beam enters the fluid, it interacts with the sample and light is radiated and fluoresced out from the fluid in various directions. By evaluating the way that the light radiates from the fluid, characteristics of the sample can be determined.

SUMMARY

In general terms, this disclosure is directed to radiated light filtering for a flow cytometer. In one possible configuration and by non-limiting example, a filter mask is provided which selectively filters light radiated by a sample.

One aspect is a filter mask for use in a flow cytometer, the filter mask comprising: a body including: light blocking features including: an outer blocker; and a secondary blocker configured to block light rays having blocked radiation angles; and light passing apertures configured to permit light rays having radiation angles greater than and less than the blocked radiation angles to pass through the body.

Another aspect is a flow cytometer comprising: a flow nozzle configured to provide a fluid along a flow path, the fluid including sample particles therein; a light source configured to generate a light beam directed toward the flow path, wherein when the light beam intersects with the flow path, light rays are radiated by the fluid and the particles at radiation angles; an optics system configured to receive the radiated light rays and to direct the light rays along an optical path, the optics assembly including at least a first filter mask, the first filter mask including light blocking features positioned in the first filter mask to selectively block light rays having specific radiation angles; and a sensor analyzer arranged at an end of the optical path to collect and analyze light rays passing through the optics system.

A further aspect is a method of evaluating a particle with a flow cytometer, the method comprising: passing a particle in a fluid along a fluid flow path; illuminating the particle and the fluid with a light beam; collecting light rays radiated from the fluid and the light beam with an optics system; selectively blocking some of the light rays having certain radiation angles with a filter mask; selectively passing others of the light rays with the filter mask; and detecting light rays passed by the filter mask with a sensor analyzer to evaluate at least one characteristic of the particle.

DETAILED DESCRIPTION

Figure 1:
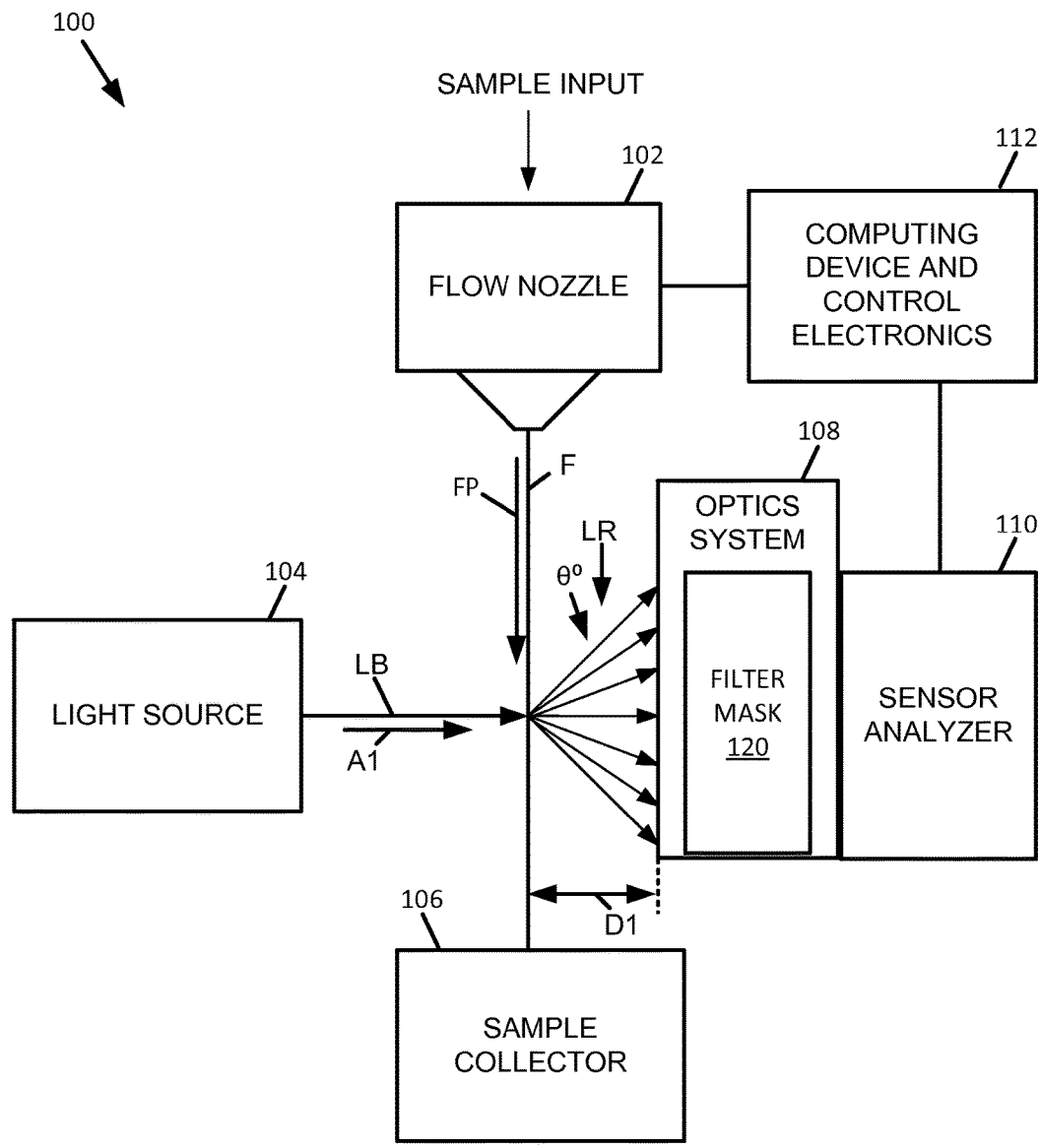
FIG. 1 is a schematic block diagram of an example flow cytometer according of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic block diagram of an example flow cytometer 100. In this example, the flow cytometer 100 includes a flow nozzle 102, a light source 104, a sample collector 106, an optics system 108, a sensor analyzer 110, and a computing device and control electronics 112. The optics system 108 includes a filter mask 120.

The flow nozzle 102 receives a sample containing particles for analysis by the flow cytometer 100. The flow nozzle 102 has a small aperture that permits only one or a small number of particles to pass through at a time, such as to arrange the particles so that they pass through the flow nozzle 102 in single file, for example. Examples of flow nozzles 102 include a flow cell and a jet-in-air nozzle. In some embodiments, the flow cell includes a transparent body including a microscopically thin channel. The fluid stream containing the particles is directed by the walls of the channel along the fluid path extending through the flow cell and past the light source 104. In other embodiments a jet-in-air nozzle is used to eject the fluid stream along the fluid path. Hydrodynamic forces cause the fluid to flow in a continuous fluid stream and confine the particles as they pass the light source 104. Other embodiments utilize other flow nozzles 102.

The sample is mixed with a sheath fluid, and the resulting fluid steam F containing the sample is directed along a flow path FP. The sample can be of a variety of different types, and some embodiments will include multiple types within a single sample. Examples of types of sample particles include beads, blood, bacteria, yeast, plankton, microparticles (e.g., from plasma membrane of cells), and mitochondria.

The light source 104 generates a light beam LB. An example of a light source 104 is a laser, which generates a laser beam. Other embodiments use other light sources, such as an arc lamp. The light beam LB is directed to the fluid path FP in a direction A1 where the light beam LB enters the fluid. Although the light beam LB is typically directed toward the fluid path FP by the light source 104 itself, the light beam LB can alternatively be directed by one or more optic devices, such as lenses, mirrors, prisms, and the like, in other embodiments after the light beam is emitted from the light source 104.

The fluid stream F is directed to a sample collector 106 after proceeding along the fluid path FP. In some embodiments, the sample collector 106 is a waste receptacle. In other embodiments, the sample collector 106 includes one or more storage receptacles. In another possible embodiment, the flow cytometer 100 is a sorting flow cytometer, and the sample collector 106 operates to sort the particles in the fluid into multiple receptacles based on one or more detected characteristics of the particles.

When the light beam LB enters the fluid stream F, at least some of the light rays LR are radiated (e.g., forward, side, or back) by the particles within the fluid. Some of these light rays are forward-scattered, as shown in FIG. 1, while other light rays are side-scattered and back-scattered. Fluoescent light is also generated, which can also radiate in forward, side, or backward directions. A radiation angle θ (sometimes also referred to as a scatter angle) is the angle of a light ray LR relative to the direction A1 of the light beam LB after being scattered or fluoresced by the fluid stream F. Because the light beam LB includes many light rays LR that can be separately radiated in different directions, different light rays LR can be radiated in different directions—having different radiation angles θ—simultaneously. Forward-scattering (and fluorescence) is illustrated and described in more detail with reference to FIG. 2. Although FIG. 1 illustrates only a vertical radiation angle θ, the light rays LR can also be radiated in a horizontal dimension (i.e., in all three dimensions).

An optics system 108 is positioned adjacent the fluid path FP to receive the radiated light rays. In some embodiments, the optics system 108 includes a filter mask 120. The filter mask 120 is arranged and configured to block a portion of the light rays LR having certain radiation angles θ and to pass another portion of the light rays having different radiation angles θ. Examples of filter mask 120 are described herein.

As discussed above, at least a portion of the optics system 108 is typically arranged adjacent the fluid path FP. In the illustrated example, the optics system 108 is positioned a distance D1 away from the fluid path. Different embodiments can have different distances D1. Some embodiments have a distance in a range from about 10 mm to about 15 mm, for example.

After the light rays LR have passed through the optics system 108, they are detected by the sensor analyzer 110. The sensor analyzer 110 detects various characteristics of the light rays, such as one or more of the magnitude and position of the detected light, time duration of the light pulse as a particle traverses the light beam, the shape of the pulse, polarization, and wavelength.

The computing device and control electronics 112 interact with the sensor analyzer 110 to evaluate characteristics of the particles in the fluid. In some embodiments, the computing device 112 includes a display, and generates a user interface on the display to convey information regarding the characteristics of the particles in the fluid to a user. The computing device 112 typically includes at least one processing device (such as a central processing unit) and at least some form of computer readable media, such as computer readable storage media. Examples of computer readable media are described herein.

In some embodiments, the flow cytometer 100 is a sorting flow cytometer in which the computing device and control electronics 112 operate to sort particles into multiple different receptacles in the sample collector 106 based at least in part on the forward-radiated light detected by the sensor analyzer 110. For example, drops of the fluid are selectively charged by the flow nozzle 102 prior to separation from the fluid stream at the flow nozzle 102 based on detected characteristics of the particles contained in the drops. The drops are then sorted into different receptacles by passing the drops through charged plates at the sample collector 106. The charged plates deflect the drops into the appropriate receptacles.

Figure 2:
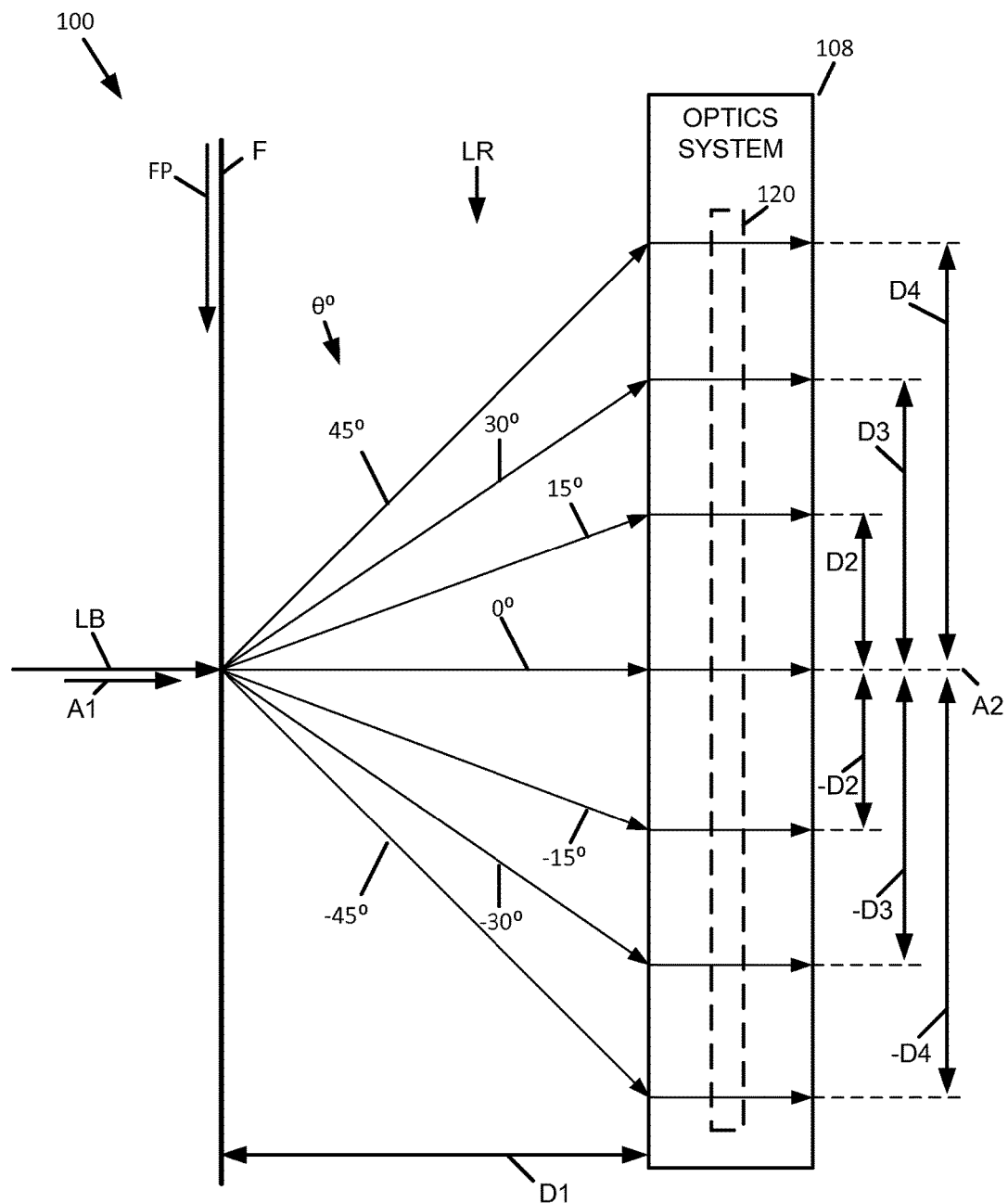
FIG. 2 is a schematic diagram illustrating a side view of a portion of the example flow cytometer shown in FIG. 1.

FIG. 2 is a schematic diagram illustrating a side view of a portion of an example flow cytometer 100, such as a portion of the flow cytometer 100 illustrated in FIG. 1. The illustrated portion of the flow cytometer 100 depicts the light beam LB, fluid stream F, light rays LR radiated by the fluid stream F, and the optics system 108. In this example, the optics system 108 includes the filter mask 120.

When the light beam LB enters the fluid stream F, the fluid (and any particles contained in the fluid) cause the light rays LR to radiate in different directions (depicted by the radiation angles θ). The radiation occurs both vertically and horizontally. The vertical radiation is illustrated in FIG. 2, which illustrates light rays LR being vertically radiated between 45° (upward) and −45° (downward). The radiation also occurs horizontally, such as between −12° (left from the perspective of the light beam LB) and +12° (right). The radiation can also occur outside of these ranges, and some embodiments collect, filter, and/or evaluate light rays LR outside of these ranges.

It has been found, however, that not all of the radiated light rays LR are equally informative when evaluating one or more characteristics of a sample. Therefore, a filter mask 120 can be used to selectively block certain portions of the light rays, while permitting the light rays of interest to pass through.

As one hypothetical example, suppose that the only light rays of interest are those having a radiation angle θ from 20° to 35°, and from −20° to −35°. A filter mask 120 can be arranged and configured to block the undesired portion of the light rays (such as those having radiation angles between −20° and +20°, and those having radiation angles greater than +/−35°). The filter mask 120 can be similarly arranged and configured with apertures formed at precise locations that permit light rays LR having radiation angles θ of interest (such as those having radiation angles θ from 20° to 35°, and from −20° to −35°) to pass through.

In some embodiments, the light rays LR are collected and redirected along an optical path by the optics system 108 before being filtered by the filter mask 120. For example, in some embodiments the optics system 108 includes one or more lenses which collect the light rays LR and direct the light rays LR along the optical path.

Even though the directions of the light rays LR can change in the optics system, it is convenient to refer to the light rays by their radiation angles—the angles from which the light rays were radiated by the fluid.

Several exemplary light rays are shown in FIG. 2. Light rays that are not radiated by the fluid continue along the axis A2 of the optical path, while light rays that were radiated are spaced from the axis A2. For example, some light rays may have a radiation angle of 15°, while other light rays may be radiated at other angles, such as 30°, 45°, −15°, −30°, and −45° and other angles therebetween, and yet other angles greater than +/−45°. The light rays that have larger radiation angles are spaced a greater distance away from the axis A2 than light rays that have smaller radiation angles. In the illustrated example, the light rays radiated at +/−15° radiation angles are spaced a distance +/−D2 away from the axis A2 at a given point in the optics system 108 (such as a distance D1 from the fluid steam F). Similarly, the light rays radiated at +/−30° and +/−45° are spaced a distance +/−D3 and +/−D4, respectively from the axis A2. The distance D4 is greater than the distance D3, which is greater than the distance D2. In some embodiments, the values of D2, D3, and D4 can be computed using basic trigonometry knowing the radiation angle of the light ray and the distance D1. In other embodiments, a transfer function is used to map between the radiation angles and the positions of the light rays, as discussed herein. The distances D2, D3, and D4 can change as the light rays pass through the optics system (such as caused by divergence or convergence of the light rays by the lenses of the optics system), but the relative positions of the light rays remain the same, in some embodiments.

As a result of this a filter mask 120 can be positioned in the optics system 108 to filter the light rays according to their radiation angles—to block certain light rays, while allowing other light rays to pass therethrough. Examples of filter masks 120 are illustrated and described with reference to FIGS. 3-9.

The light rays that pass through the filter mask 120 are then collected by the optics system 108 and directed to the sensor analyzer 110, where the one or more characteristics of the sample are evaluated.

A benefit of the configuration shown in FIG. 2 is that precise filtering of light rays LR having particular radiation angles can be accomplished, limited primarily by the ability to precisely form apertures in the filter mask 120, and the ability to properly position the filter mask 120 with respect to the light beam LB direction A1.

Another benefit is that filter masks can be selected for use within the flow cytometer which have desired characteristics that are optimized for a particular application. For example, a first filter mask can be inserted into the optics system, which has a first set of characteristics that make it useful for a first application. The filter mask can then be removed and replaced with a different filter mask for a second application. In some embodiments, no changes need to be made to the optics system 108, other than to remove the filter mask and replace it with another filter mask having the desired characteristics. Additional examples are described herein.

Figure 3:
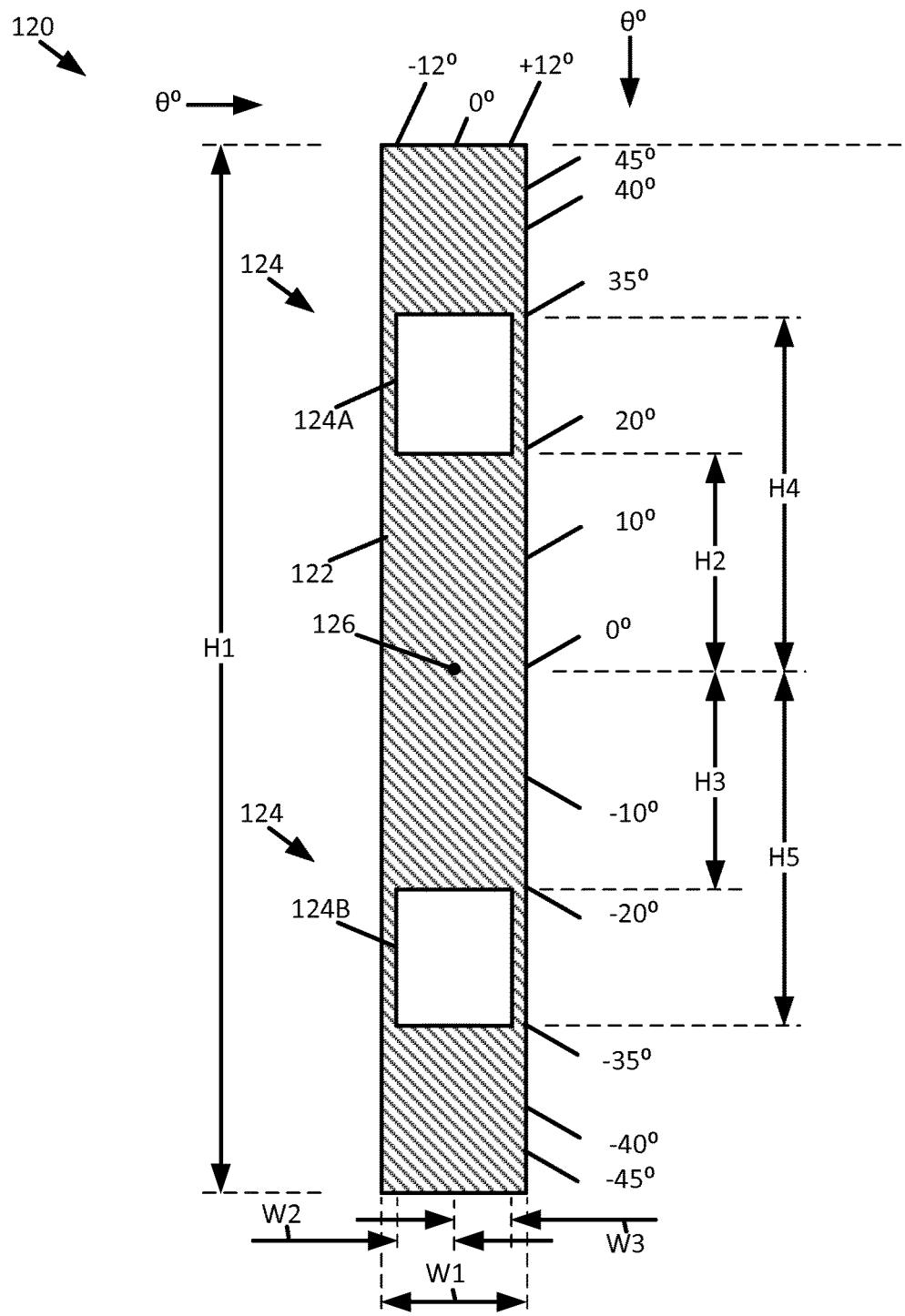
FIG. 3 is a front elevational view of an example filter mask.

FIG. 3 is a front elevational view of an example filter mask 120. In this example, the filter mask 120 includes a body 122, apertures 124, and an origin point 126.

The body 122 of the filter mask 120 is arranged and configured to block certain portions of the radiated light rays LR from passing. For example, in some embodiments the mask body 122 is formed of a material that will absorb most or all of the light rays LR. The filter mask 120 can be formed of a material such as plastic or metal, for example. In another possible embodiment, the body is formed of one material and is coated with one or more layers of material that absorb most or all of the light rays LR. For example, in some embodiments the body is formed of glass. A coating is applied to one surface of the glass, and photolithography techniques are utilized to selectively remove the coating to form apertures 124 through the coating. In this example, the apertures 124 do not extend entirely through the mask body 122, but only through the coating, but due to the transparency of the glass, the apertures 124 still permit light rays to pass therethrough. The photolithography techniques can include, for example, masking of the light-blocking portions of the body 122, and etching of the coating from the aperture 124 portions that are not protected by the masking layer.

The actual physical dimensions of the filter mask 120 are selected depending on the desired location of the filter mask within the optics system 108, and the known relative positions of the light rays having various different radiation angles, as shown in FIG. 2 (e.g., distances D2, D3, and D4). The overall height H1 and width W1 are selected to be large enough to block the undesired light rays from proceeding along the optical path.

In some embodiments, the filter mask 120 is positioned in the optical path at a location where the unradiated light rays (axis A2, shown in FIG. 2) are directed toward an origin point 126 of the filter mask 120. The origin point 126 is the point of the filter mask 120 at which the unradiated light rays are directed when the filter mask 120 is properly positioned within the optics system 108.

The filter mask 120 shown in FIG. 3 includes apertures 124 (including apertures 124A and 124B in this example) formed in the body 122. The apertures 124 are positioned at particular locations in the body 122 to permit radiated light rays LR having certain radiation angles θ to pass therethrough. In this example, the apertures are positioned to permit light rays LR having a vertical radiation angle between +/−20° and +/−35° and a horizontal radiation angle between −12° and +12° to pass therethrough. Accordingly, aperture 124A has a inner edge that is spaced a distance H2 from the origin point 126, corresponding to the anticipated position of light rays having a radiation angle of 20°. An outer edge of the aperture 124A is spaced a distance H4 from the origin point 126, corresponding to the position of light rays having a radiation angle of 35°. A left edge of the aperture 124A (from the perspective of the light beam) is positioned a distance W2 toward the left of the origin point 126, and a right edge of the aperture 124A is positioned at an equal distance W3 to the right of the origin point 126, corresponding to the horizontal radiation angles of +/−12°. The aperture 124B is similarly positioned having an inner edge a distance H3 and an outer edge a distance H5 away from the origin point 126 in the opposite (i.e., negative) direction, and having the same left and right edge positions.

In some embodiments, the specific positions of the filter mask 120 apertures are determined using a transfer function. The transfer function maps the radiation angles to the appropriate physical positions within the optics system. In some embodiments, the radiation angles are linearly related to the physical positions of the filter mask features. In other embodiments, the transfer function may be non-linear, such as having a logarithmic, parabolic, or other non-linear relationship. In such embodiments, the transfer function can be determined according to the specific characteristics of the optics system to permit mapping between the radiation angles and the physical positions for desired features of the filter masks.

Figure 4:
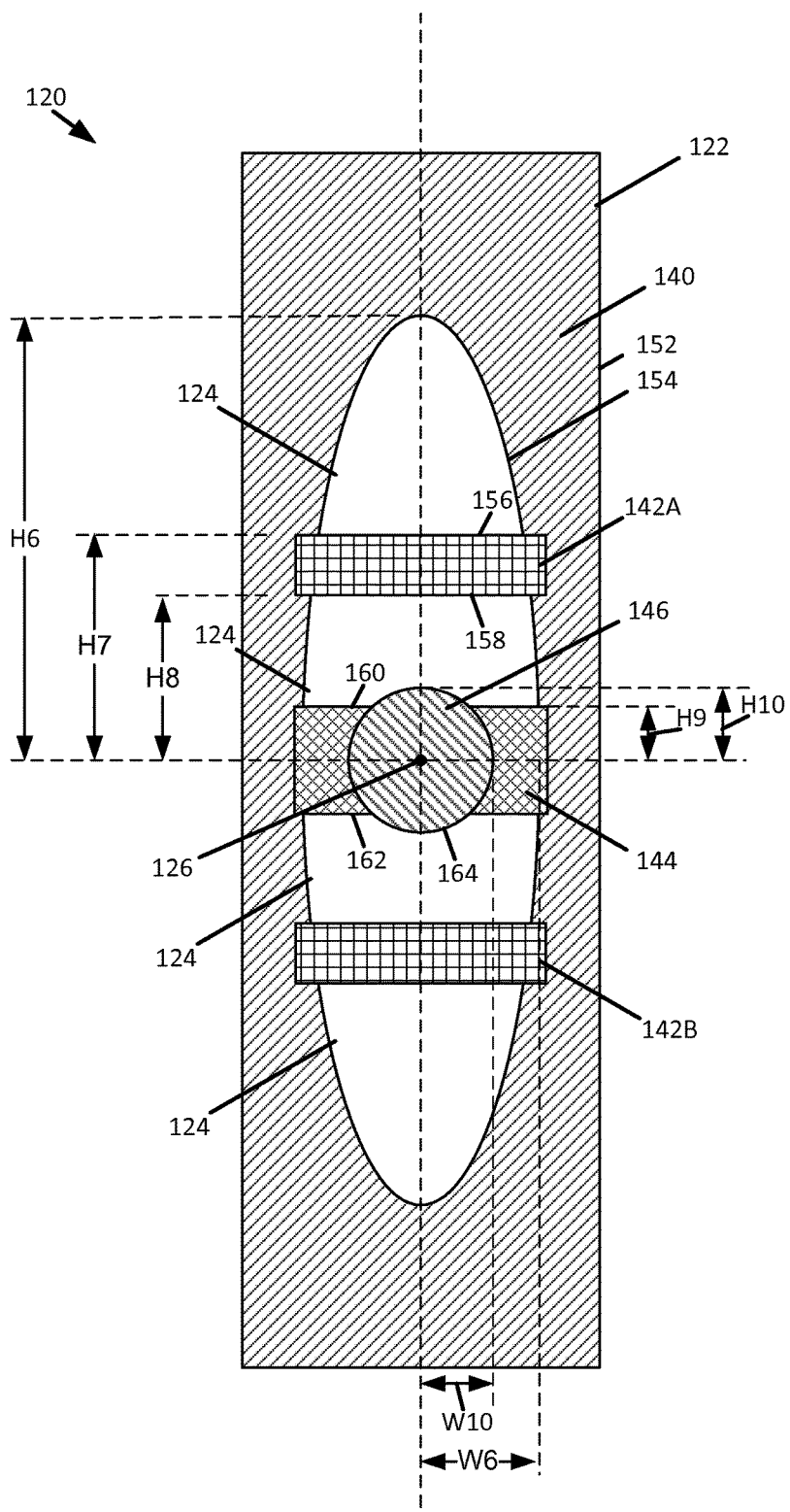
FIG. 4 is a front elevational view of another example filter mask.

FIG. 4 is a front elevational view of another example filter mask 120. In this example, the filter mask 120 includes a body 122 and apertures 124. The body 122 includes four exemplary light blocking features, including an outer blocker 140, a secondary blocker 142, a central blocker 144, and a bullseye blocker 146. Not all embodiments include all four features. For example, some embodiments include one, two, or three of these features.

As discussed herein, the body 122 is typically formed of a thin sheet of one or more materials, such as plastic, metal, or glass. In some embodiments, the body 122 includes a coating of one or more layers of one or more other materials. The body 122 operates to block light rays having certain radiation angles, while including apertures 124 that permit other light rays to pass therethrough. In some embodiments, the blocking portions of the body 122 are formed of a material that substantially absorbs and/or blocks light rays, such as a material having a dark color (e.g., black).

Apertures 124 are formed in the body 122 to permit light to pass therethrough. The apertures 124 can extend entirely through the body 122, or through one or more layers of light absorbing and/or blocking material. In some embodiments, the apertures 124 are transparent.

Each of the four exemplary features of the body 122 are described in turn below.

The outer blocker 140 is configured to block out light rays having radiation angles greater than desired maximum vertical and horizontal radiation angles. In this example, the outer blocker 140 includes an outer edge 152 and an inner edge 154, and the outer blocker 140 extends therebetween. The outer blocker 140 has a height and width (i.e., similar to H1 and W1, shown in the example of FIG. 3) that are suitable to block light rays having radiation angles greater than the maximum vertical and horizontal radiation angles from proceeding along the optical path. In some embodiments, the outer edge 152 of the outer blocker 140 is coupled to a cartridge housing, which is supported by a frame of the flow cytometer 100 at a location along the optical path. When the filter mask 120 is installed in the flow cytometer 100, the filter mask 120 is positioned so that the origin point 126 is aligned with an axis A2 (shown in FIG. 2) of the optical path.

The inner edge 154 of the outer blocker 140 defines the outer peripheries of the apertures 124, and therefore defines the maximum radiation angles that may proceed along the optical path. In this example, the inner edge 154 is elliptical. Other embodiments have other shapes, such as circular, square, or rectangular. The half height H6 of the inner edge 154 defines the maximum vertical radiation angle of light rays that are permitted to pass through the filter mask 120. The half width W6 of the inner edge 154 defines the maximum horizontal radiation angle of light rays that are permitted to pass through the filter mask 120. Typically the filter mask 120 is vertically and horizontally symmetrical. Asymmetrical filter masks can also be formed in other embodiments.

Figure 5:
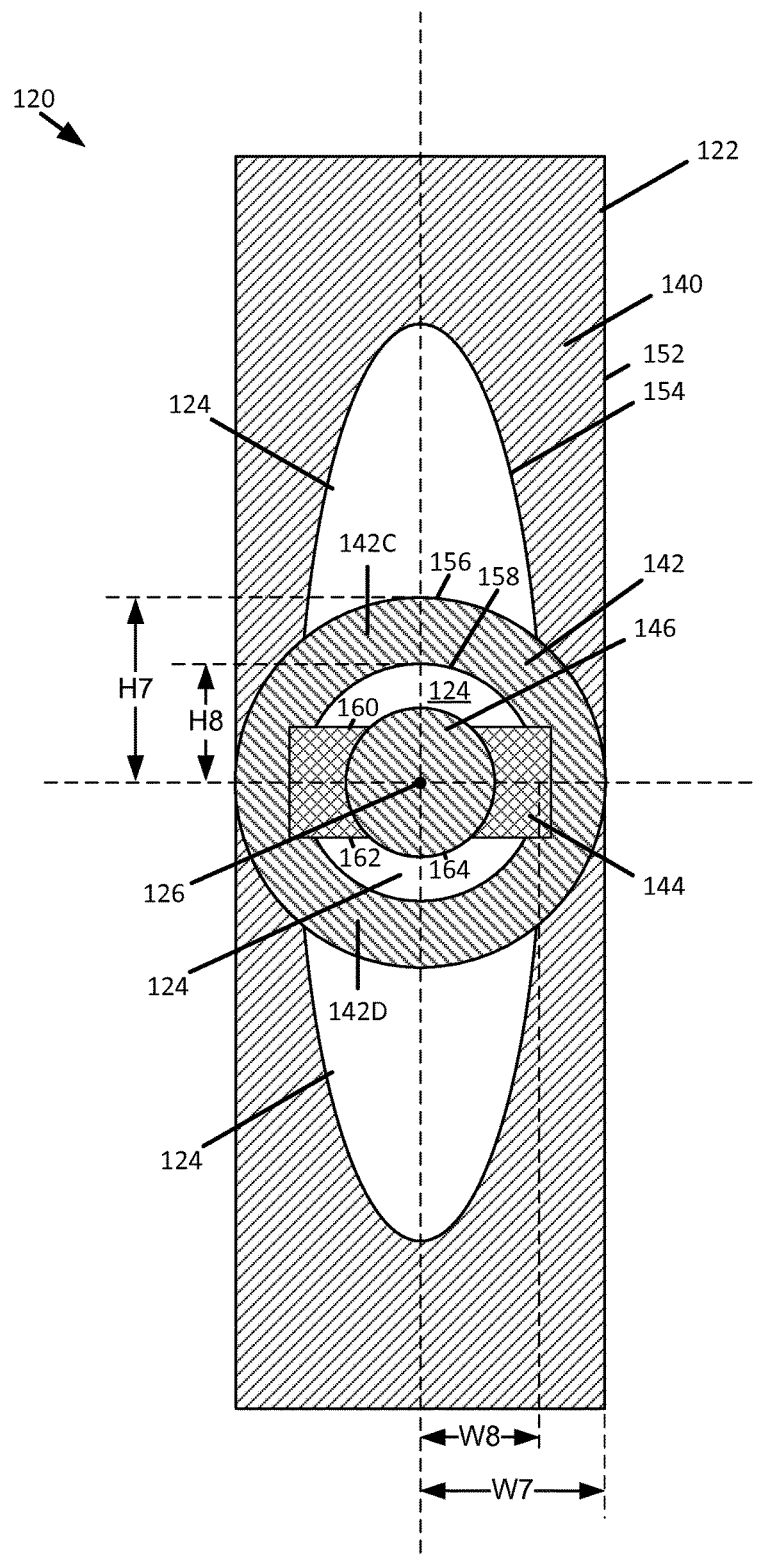
FIG. 5 is a front elevational view of another example filter mask.

The secondary blocker 142, which includes portions 142A and 142B in some embodiments, is arranged at a location between the origin point 126 and the inner edge 154 of the outer blocker 140, to block a portion of the light rays that would otherwise pass through the outer blocker 140. The secondary blocker 142 can be formed in a linear or a radial configuration. The example in FIG. 4 illustrates the linear configuration including linear secondary blocker 142. The example in FIG. 5 illustrates the radial configuration, including radial secondary blocker portions 142C and 142D.

With continued reference to the example shown in FIG. 4, the secondary blocker 142 has a rectangular shape that extends horizontally between the inner edge 154 of the outer blocker 140. The secondary blocker portion 142A includes an outer edge 156 and an inner edge 158. The outer edge 156 is positioned at a height H7 from the origin point 126 and the inner edge is positioned at a height H8 from the origin point 126. The secondary blocker portion 142A extends therebetween, and is configured to block light rays having radiation angles causing the light rays to pass between heights H7 and H8 along the optical path. The thickness of the secondary blocker 142 is the difference between height H7 and height H8, which is less than the height H6 of the inner edge 154. The secondary blocker portion 142B typically has the same shape as the secondary blocker portion 142A, and is arranged at an opposite side of the filter mask 120. Apertures 124 positioned above and below the secondary blocker permit light rays of different radiation angles to pass above and below each of the secondary blocker portions 142A and 142B. In some embodiments, light rays LR of different radiation angles (both greater than and less than the angles blocked by the secondary blocker) are permitted to pass through apertures 124 of the filter mask and are collected and analyzed by a single sensor analyzer (as shown in FIG. 1).

The central blocker 144 extends horizontally through the origin point 126 and between opposite sides of the inner edge 154 of the outer blocker 140, to block a portion of the light rays that have less than a minimum vertical radiation angle. In this example, the central blocker 144 is rectangular having outer edges 160 and 162. The outer edges 160 and 162 extend horizontally and are positioned a height H9 away from the origin point 126. In other embodiments, the edges 160 and 162 are curved, such as having a arcuate, partial circular, or parabolic shape.

The bullseye blocker 146 is typically centered around the origin point 126 and is configured to block light rays having a magnitude of less than a minimum radiation angle. In some embodiments the bullseye blocker 146 has a circular shape. Other embodiments have other shapes, such as elliptical, square, or rectangular. The bullseye blocker has an outer edge 164. In this example, the outer edge 164 has a half height H10 and a half width W10. When the bullseye blocker has a circular shape, the height H10 and width W10 are equal to the radius of the circular shape. The bullseye blocker 146 operates to block light rays from the light beam that are not radiated by the fluid, as well as those that have a radiation angle of less than the minimum radiation angle. By blocking this bright portion of the light rays, the signal to noise ratio can be significantly improved, for example. However, a similar function can also or alternatively be performed by the central blocker 144 in some embodiments.

FIG. 5 is a front elevational view illustrating another example of a filter mask 120. The filter mask shown in FIG. 5 is generally the same as that shown in FIG. 4, except that in this example the secondary blocker 142 has a radial configuration. Accordingly, the descriptions of the filter mask 120, body 122, outer blocker 140, central blocker 144, and bullseye blocker 146 are not repeated here.

In this example, the secondary blocker 142 has a radial configuration including secondary blocker portions 142C and 142D, and includes an outer edge 156 and an inner edge 158. The secondary blocker 142 extends between the outer edge 156 and the inner edge 158.

In some embodiments, the edges 156 and 158 have a circular shape. Other embodiments have other shapes, such as elliptical, square, or rectangular. The outer edge 156 has a height H7 and a width W7. The inner edge 158 has a height H8 and a width W8.

Figure 6:
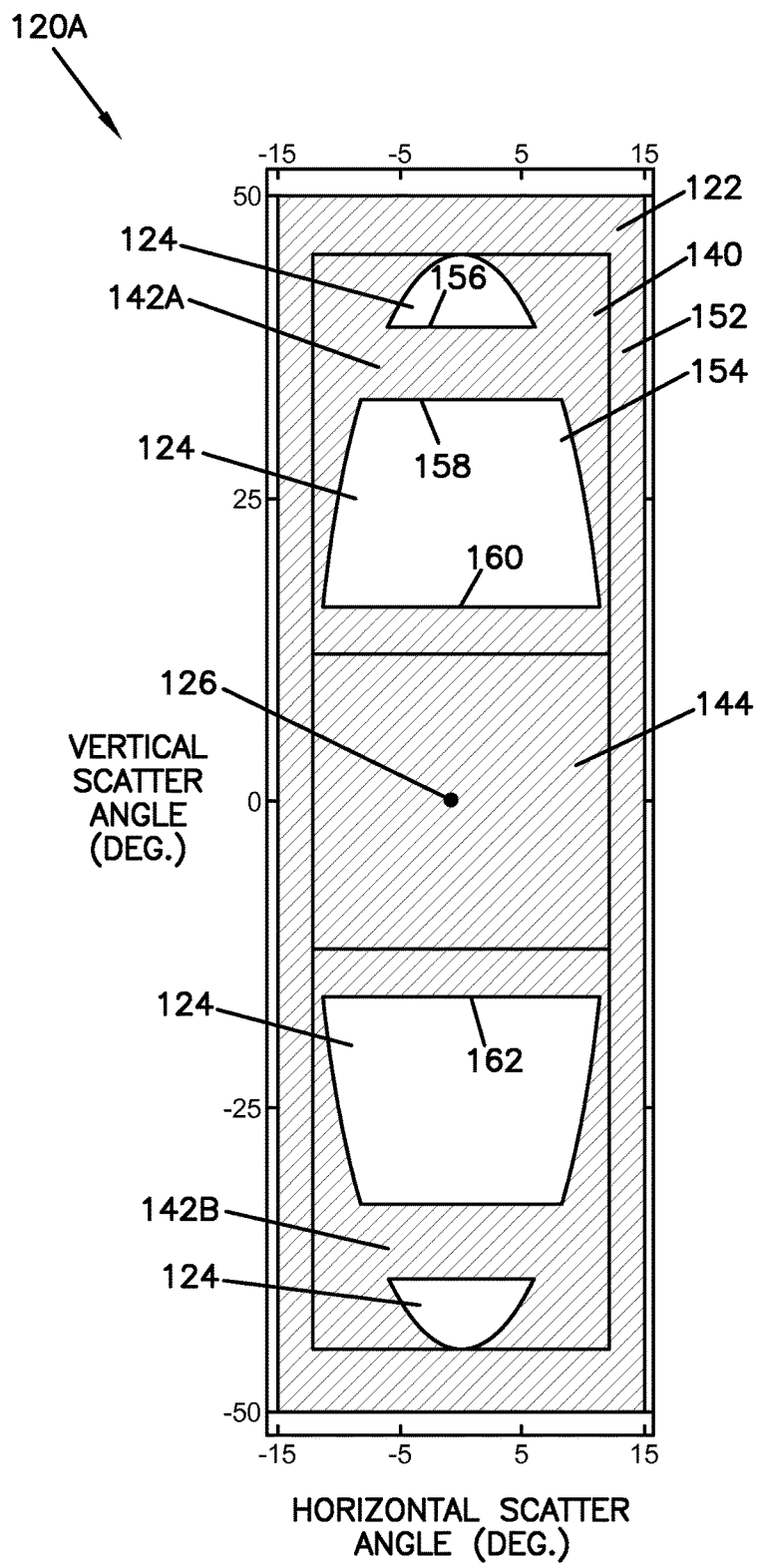
FIG. 6 is a front elevational view of another example filter mask.
Figure 7:
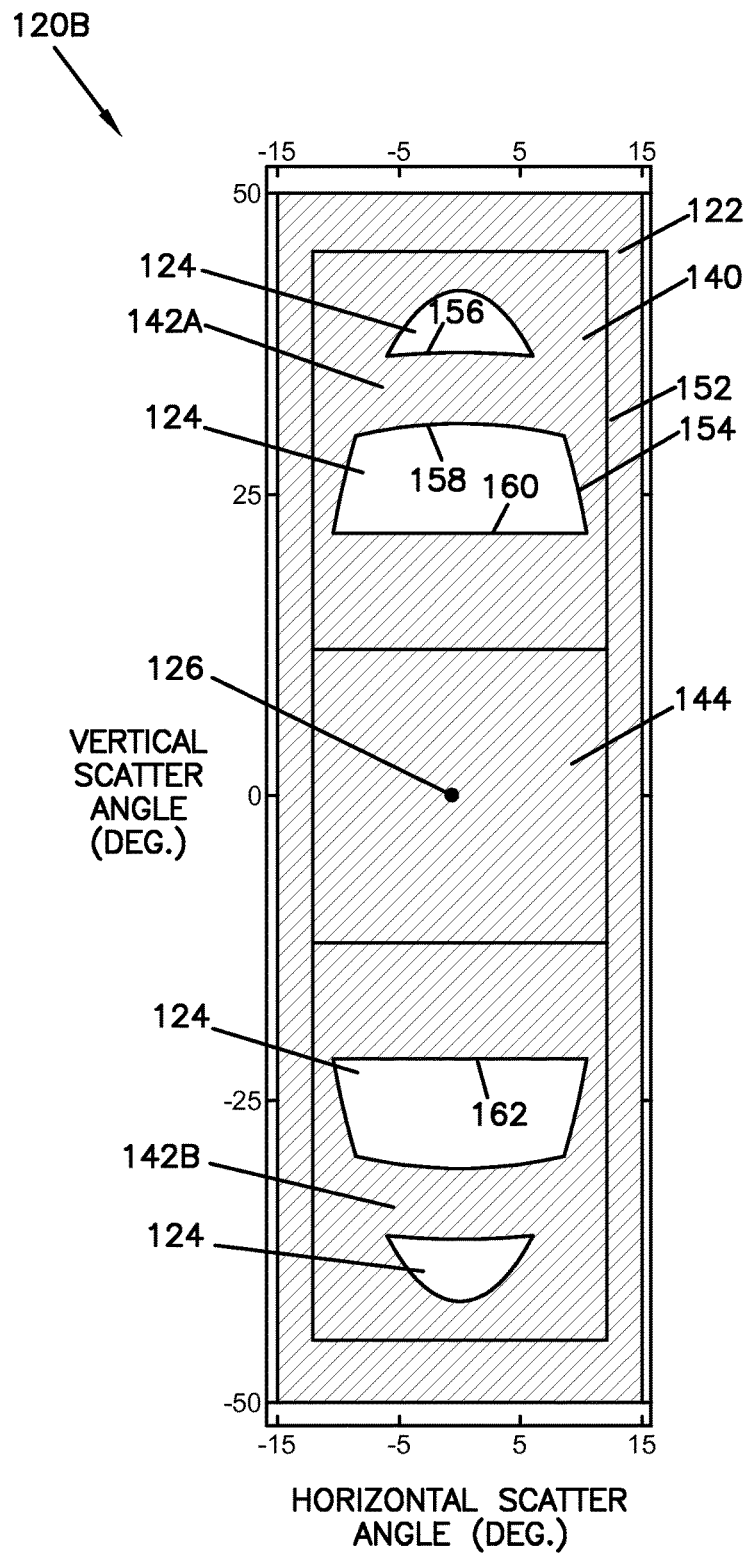
FIG. 7 is a front elevational view of another example filter mask.
Figure 8:
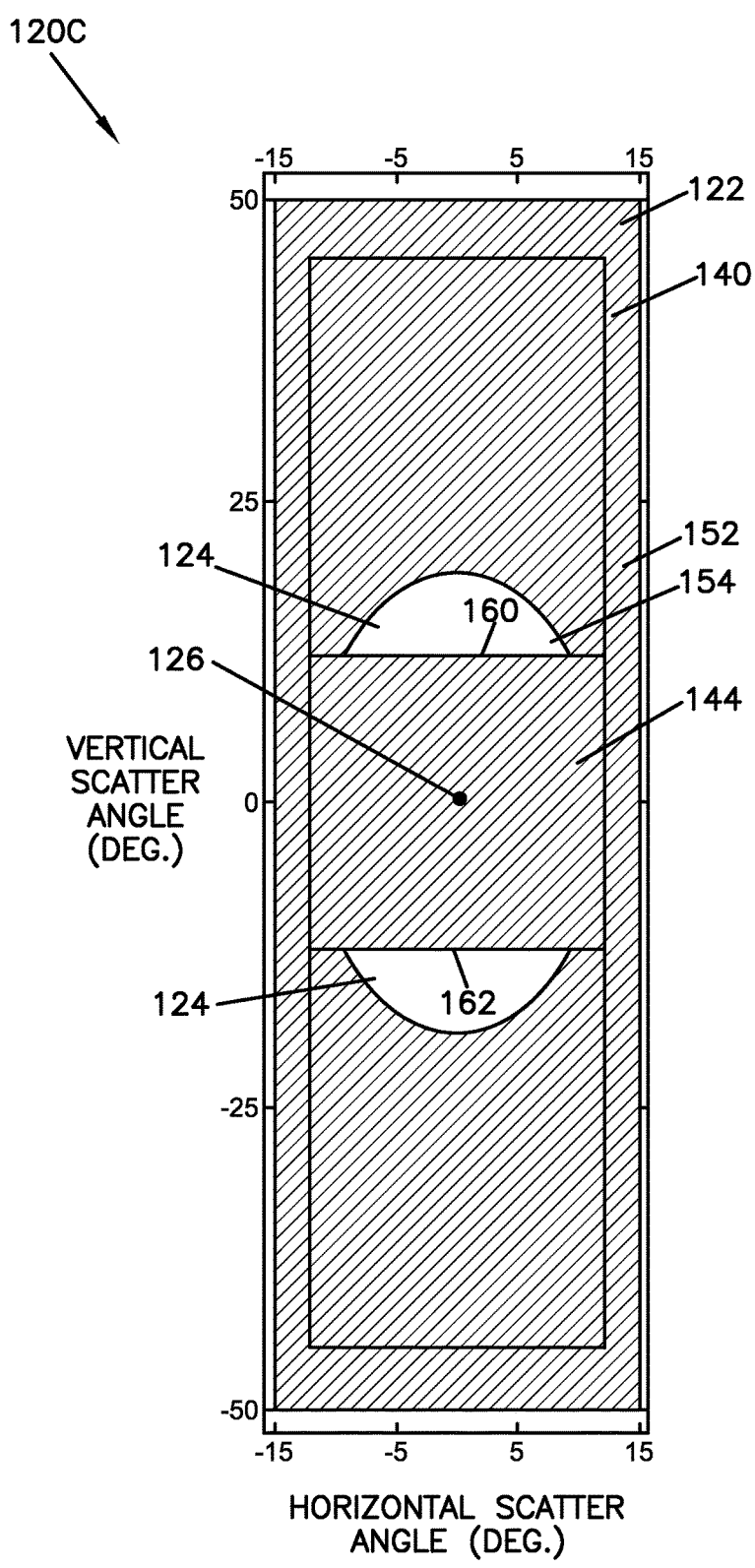
FIG. 8 is a front elevational view of another example filter mask.
Figure 9:
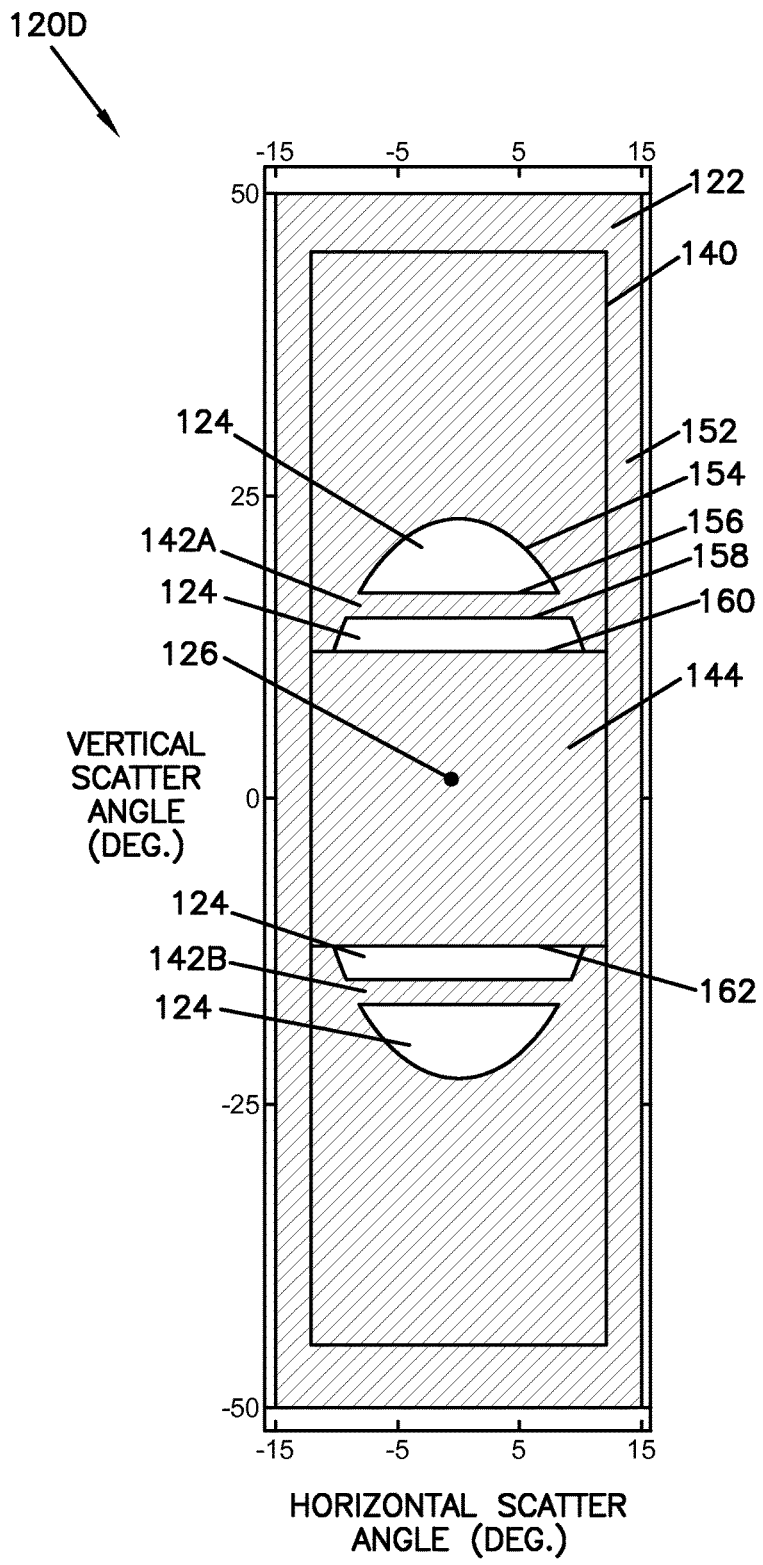
FIG. 9 is a front elevational view of another example filter mask.

FIGS. 6-9 illustrate several additional examples of filter masks 120. FIGS. 6-7 illustrates a first category of filter masks referred to as smoothness masks. FIGS. 8-9 illustrate a second category of filter masks referred to as separation masks.

FIG. 6 is a front elevational view of an example filter mask 120A. The example filter mask 120A includes a body 122 and apertures 124. The body 122 includes an origin point 126, an outer blocker 140, a secondary blocker 142, and a central blocker 144. Filter mask 120A is a first example of a smoothness mask.

As discussed herein, the physical dimensions of the filter mask 120 can be described in terms of radiation angles of light rays, because the radiation angles correspond to particular physical positions within the optical path. The radiation angles are proportional to the actual physical dimensions, which can be computed based on the specific physical location of the filter mask 120 in the optics system 108. Therefore, FIG. 6 identifies the scale of the example filter mask 120A according to vertical (−50° to +50°) and horizontal (−15° to +15°) radiation angles, and such angles are further discussed below.

The outer blocker 140 has an outer edge 152. In this example, the outer edge is positioned at vertical radiation angles of +/−50° and at horizontal radiation angles of +/−15°.

The outer blocker 140 also has an inner edge 154 having an elliptical shape. The top and bottom of the inner edge 154 are positioned at the vertical radiation angles of +/−45°, and the sides of the inner edge 154 are positioned at the vertical radiation angles of +/−12°.

In this example, the secondary blocker 142 is a linear secondary blocker. The secondary blocker 142 includes portions 142A and 142B, each having outer edges 156 and inner edges 158. The outer edges 156 are arranged at the vertical radiation angles of +/−39°, and the inner edges 158 are arranged at the vertical radiation angles of +/−33°.

The central blocker 144 has outer edges 160 and 162. The outer edges 160 and 162 are arranged at the vertical radiation angles of +/−16°.

FIG. 7 is a front elevational view of an example filter mask 120B. The example filter mask 120B includes body 122 and apertures 124. The body 122 includes an origin point 126, an outer blocker 140, a secondary blocker 142, and a central blocker 144. Filter mask 120B is a second example of a smoothness mask.

The outer blocker 140 has an outer edge 152. In this example, the outer edge is positioned at vertical radiation angles of +/−50° and at horizontal radiation angles of +/−15°.

The outer blocker 140 also has an inner edge 154 having an elliptical shape. The top and bottom of the inner edge 154 are positioned at the vertical radiation angles of +/−42°, and the sides of the inner edge 154 are positioned at the vertical radiation angles of +/−12°.

In this example, the secondary blocker 142 is a radial secondary blocker. The secondary blocker 142 includes outer edges 156 and inner edges 158. The outer edges 156 are circular having a radius that intersects with the vertical radiation angles of +/−37°, and the inner edges 158 are circular having a radius that intersects with the vertical radiation angles of +/−31°. In other words, the secondary blocker 142 is arranged and configured to block light rays having radiation angle magnitudes between 31° and 37°.

The central blocker 144 has outer edges 160 and 162. The outer edges 160 and 162 are arranged at the vertical radiation angles of +/−22°.

FIG. 8 is a front elevational view of another example filter mask 120C. The example filter mask 120C includes body 122 and apertures 124. The body 122 includes an origin point 126, an outer blocker 140 and a central blocker 144. Filter mask 120C is a first example of a separation mask.

The outer blocker 140 has an outer edge 152. In this example, the outer edge is positioned at vertical radiation angles of +/−50° and at horizontal radiation angles of +/−15°.

The outer blocker 140 also has an inner edge 154 having an elliptical shape. The top and bottom of the inner edge 154 are positioned at the vertical radiation angles of +/−19°, and the sides of the inner edge 154 are positioned at the vertical radiation angles of +/−12°.

The central blocker 144 has outer edges 160 and 162. The outer edges 160 and 162 are arranged at the vertical radiation angles of +/−12.2°.

FIG. 9 is a front elevational view of an example filter mask 120D. The example filter mask 120D includes body 122 and apertures 124. The body 122 includes an origin point 126, an outer blocker 140, a secondary blocker 142, and a central blocker 144. Filter mask 120D is a second example of a separation mask.

The outer blocker 140 has an outer edge 152. In this example, the outer edge is positioned at vertical radiation angles of +/−50° and at horizontal radiation angles of +/−15°.

The outer blocker 140 also has an inner edge 154 having an elliptical shape. The top and bottom of the inner edge 154 are positioned at the vertical radiation angles of +/−23°, and the sides of the inner edge 154 are positioned at the vertical radiation angles of +/−12°.

In this example, the secondary blocker 142 is a linear secondary blocker. The secondary blocker 142 includes portions 142A and 142B, each having outer edges 156 and inner edges 158. The outer edges 156 are arranged at the vertical radiation angles of +/−17°, and the inner edges 158 are arranged at the vertical radiation angles of +/−15°.

The central blocker 144 has outer edges 160 and 162. The outer edges 160 and 162 are arranged at the vertical radiation angles of +/−12.2°.

Figure 10:
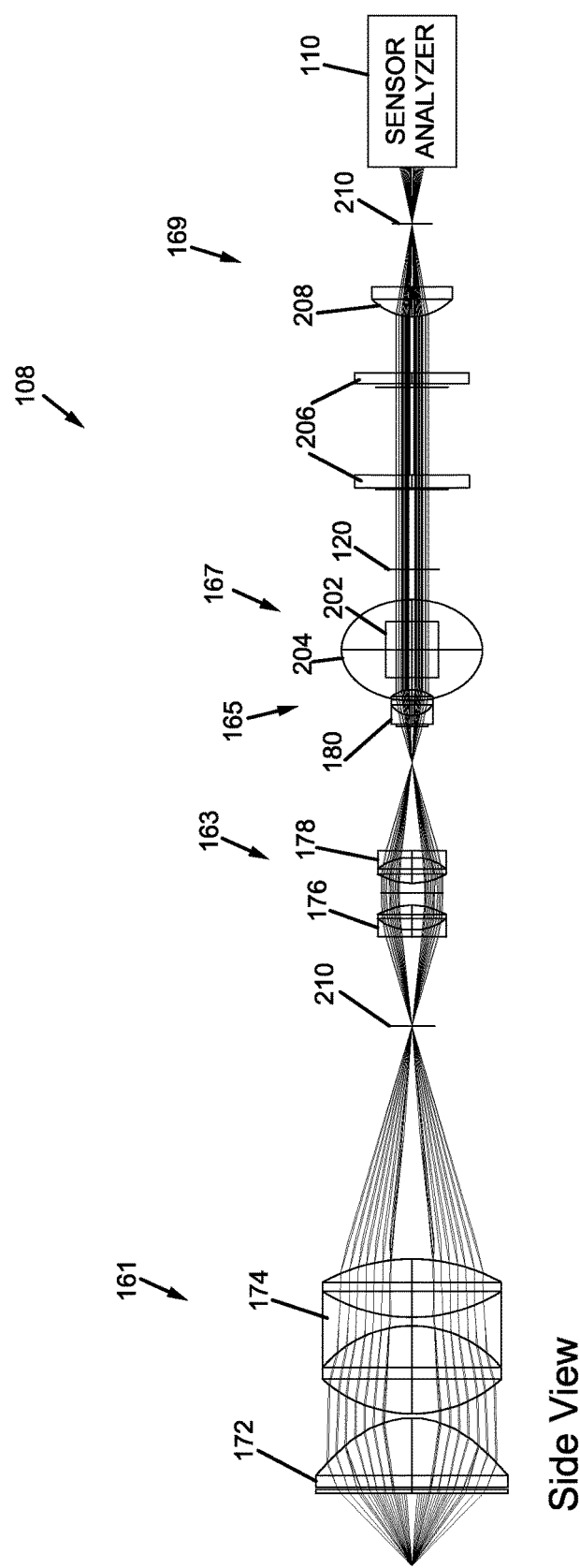
FIG. 10 is a cross sectional side view of an example optics system.
Figure 11:
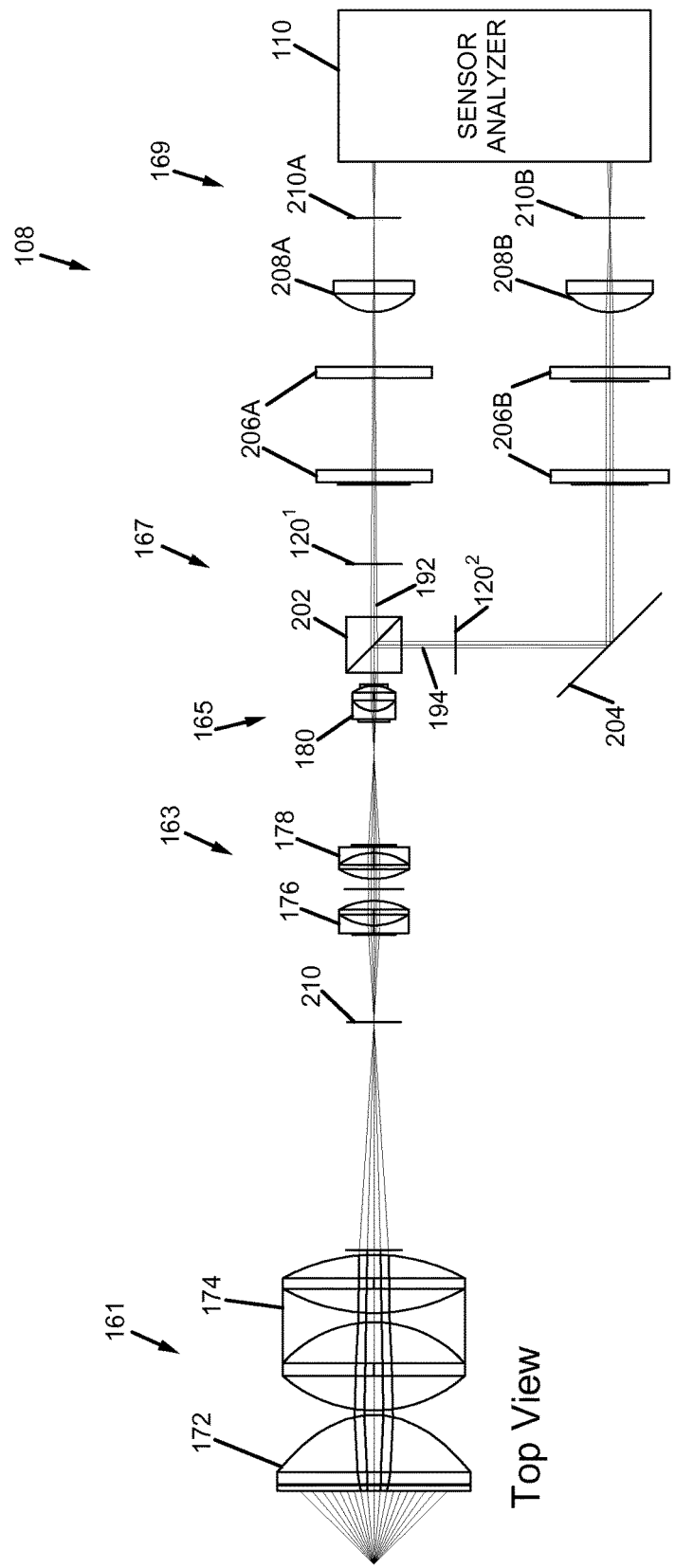
FIG. 11 is a cross-sectional top view of the example optics system shown in FIG. 11.

FIGS. 10-11 illustrate another example of the optics system 108, shown in FIG. 1. FIG. 10 is a cross-sectional side view of the example optics system 108. FIG. 11 is a cross-sectional top view of the example optics system 108.

In this example, the optics system 108 includes a collection optics assembly 161, re-imager 163, collimator 165, beam separating assembly 167, filter masks 120, as well as additional possible optical components 169.

Although this example is illustrated and described with reference to a particular physical implementation of the optics system 108, such as including particular types of lenses and particular lens configurations, other embodiments can have other configurations. Additional examples of possible optics assemblies are illustrated and described in more detail in U.S. Patent Application Ser. No. 61/793,771, titled OPTICS SYSTEM FOR A FLOW CYTOMETER, and filed on even date herewith, the disclosure of which is hereby incorporated by reference in its entirety.

In some embodiments the collection optics assembly 161 includes lens 172 and triplet 174, a re-imager 163 including doublets 176 and 178, and a collimator 165 including a doublet 180.

Additionally, some embodiments include a beam separating assembly 167 that is arranged and configured to separate the light rays into two or more separate beams, such as a beam 192 and a beam 194 (FIG. 11). In this example, the beam separating assembly 167 includes a beam splitter 202 and a mirror 204. The beam splitter 202 is positioned in the optical path of the optics system 108 and is configured such that half of the light rays are reflected toward the mirror 204, forming the beam 194 (FIG. 11), and the other half of the light rays are transmitted, forming the beam 192 (FIG. 11). In some embodiments, the mirror 204 is arranged to redirect the beam 194 toward the sensor analyzer 110, so that the beams 192 and 194 are parallel. The light rays LR can be separated into additional beams using additional beam splitters, if desired. In another possible embodiment, the mirror 204 can be omitted, such that the beam 194 continues in a direction perpendicular to beam 192, and another sensor analyzer 110 (or another portion of the sensor analyzer 110) may be positioned along the beam 194 path.

Each of the separate beams 192 and 194 can then be separately filtered and analyzed. In this example, each of the beams 192 and 194 is passed through a separate filter mask $120^1$ and mask $120^2$. The filter masks $120^1$ and $120^2$ can be the same, or they can be different. For example, the filter mask $120^1$ can be used to permit a selected portion of light rays to pass that are associated with certain radiation angles θ, and the filter mask $120^2$ can be used to permit another selected portion of light rays to pass that are associated with other radiation angles θ. In this way the sensor analyzer 110 can evaluate multiple portions of the radiated light rays separately and simultaneously for the same portion of the fluid stream F.

In one example embodiment, the filter mask $120^1$ is a smoothness mask and the filter mask $120^2$ is a separation mask. Examples of smoothness masks are illustrated in FIGS. 6-7, and examples of separation masks are illustrated in FIGS. 8-9. Smoothness and separation masks are also discussed in further detail with reference to FIGS. 12-13.

Some embodiments include one or more additional optical components 169. Examples of the additional optical components include filter components 206, lenses 208, and aperture components 210.

The filter components 206 are provided in some embodiments to further filter the light rays before they are passed to the sensor analyzer. Examples of filter components 206 include spectral filters, neutral density filters, and polarizing filters.

The lenses 208A and 208B are provided to converge the light rays to a focal point to pass the light rays through aperture components 210A and 210B. The aperture components 210A and 210B are positioned at the focal points of the lenses 208A and 208B and are configured to block stray light from the sensor analyzer. Additional aperture components 210 can similarly be included at other focal points.

In the example shown in FIG. 11, the overall path lengths of beams 192 and 194 are not equal. More specifically, because the beam 194 is offset by the beam splitter a distance equal to the distance between the beam splitter 202 and the mirror 204, the beam 194 travels a longer distance than the beam 192. In other possible embodiments, the optics system 108 is adjusted to provide equal path lengths. For example, the offset of beam 194 can be accounted for by either increasing the path length of beam 192 by an equal distance, or by decreasing the path length of beam 194 by an equal distance. As a more specific example, the distance between the filter components 206 and the lenses 208 (e.g., in the collimated or pseudo-collimated region), can be increased or decreased to provide beams 192 and 194 of equal path lengths. For instance, in some embodiments the distance between beam splitter 202 and the sensor analyzer 110 is increased (between filter components 206A and lens 208A) a distance equal to the distance between beam splitter 202 and mirror 204, so that the path lengths for beams 192 and 194 are equal. Alternatively, in another possible embodiment the distance between mirror 204 and sensor analyzer 110 can be reduced by the same distance.

Figure 12:
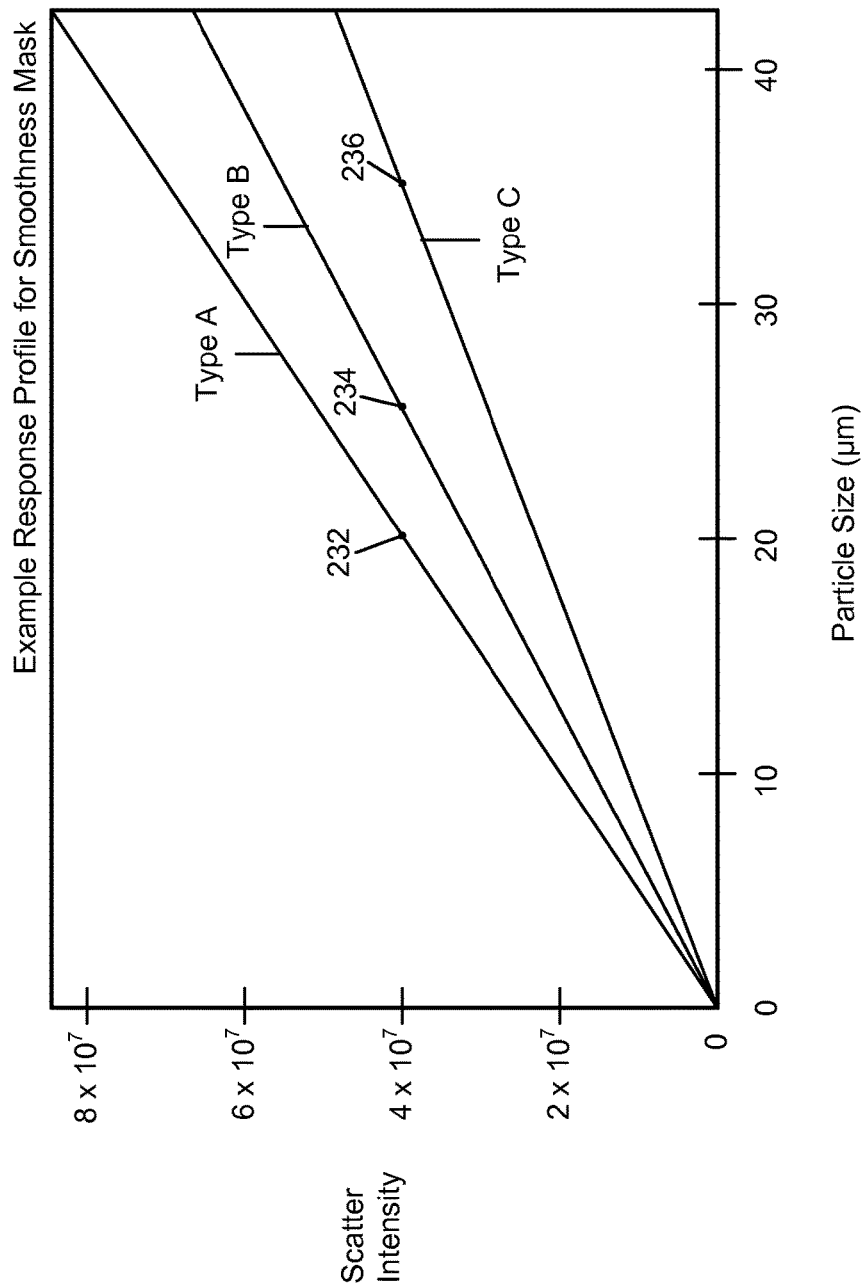
FIG. 12 is a schematic diagram illustrating an exemplary response profile for an example smoothness mask.

FIG. 12 is a schematic diagram illustrating an exemplary response profile for a smoothness mask. Some specific examples of smoothness masks are illustrated and described with reference to FIGS. 6-7. Response profiles for three different types of particles (Types A, B, and C) are illustrated. The specific data illustrated in FIG. 12 is hypothetical but provided to help illustrate the concepts discussed below.

A smoothness mask is a filter mask that, for a given type of particle, exhibits a linear, or substantially linear, response to variations in the size of particles contained within the sample. As a result, when the particle type is known, the size of the particle can be determined very precisely. FIG. 12 depicts an example of such a response. In this example, the radiation intensity increases linearly as a function of the particle size, for a given type of particle. In other words, larger particles of a particular type (e.g., Type A) result in a greater detected radiation intensity than smaller particles of the same type. Therefore, when a sample contains a single known type of particle, or a single set of particles having a common response profile, the detected radiation intensity provides a direct indication of the sizes of the particles.

A smoothness mask may be somewhat sensitive to variations in the types of particles present in a sample. For example, when a sample contains multiple different types of particles (e.g., Types A, B, and C), the filter mask may not exhibit a linear response across the multiple different types of particles. As one example, if the sensor analyzer 110 (FIG. 1) detects a radiation intensity for a given particle of $4\times10^7$, and multiple different types of particles (e.g., Types A, B, and C) are present in the sample, it is difficult for the cytometer 100 to determine the particle size based solely on the detected radiation intensity. As shown, the particle size may be 20 μm for particle Type A, 27 μm for particle Type B, or 33 μm for particle type C. As a result, a smoothness mask may cause the detected radiation intensity for a smaller particle of a first type (e.g., a 20 μm particle of Type A) to be greater than the radiation intensity detected for a larger particle of a second type (e.g., a 30 μm particle of Type C). In this scenario, it can be difficult to determine the relative or actual sizes of the particles based solely on the radiation intensity detected when using a single smoothness mask.

In some embodiments, the smoothness mask is selected to minimize ripple, resulting in a reduced path length for the scatter intensity function. The minimum path length possible is a straight line, such as illustrated in FIG. 12.

Figure 13:
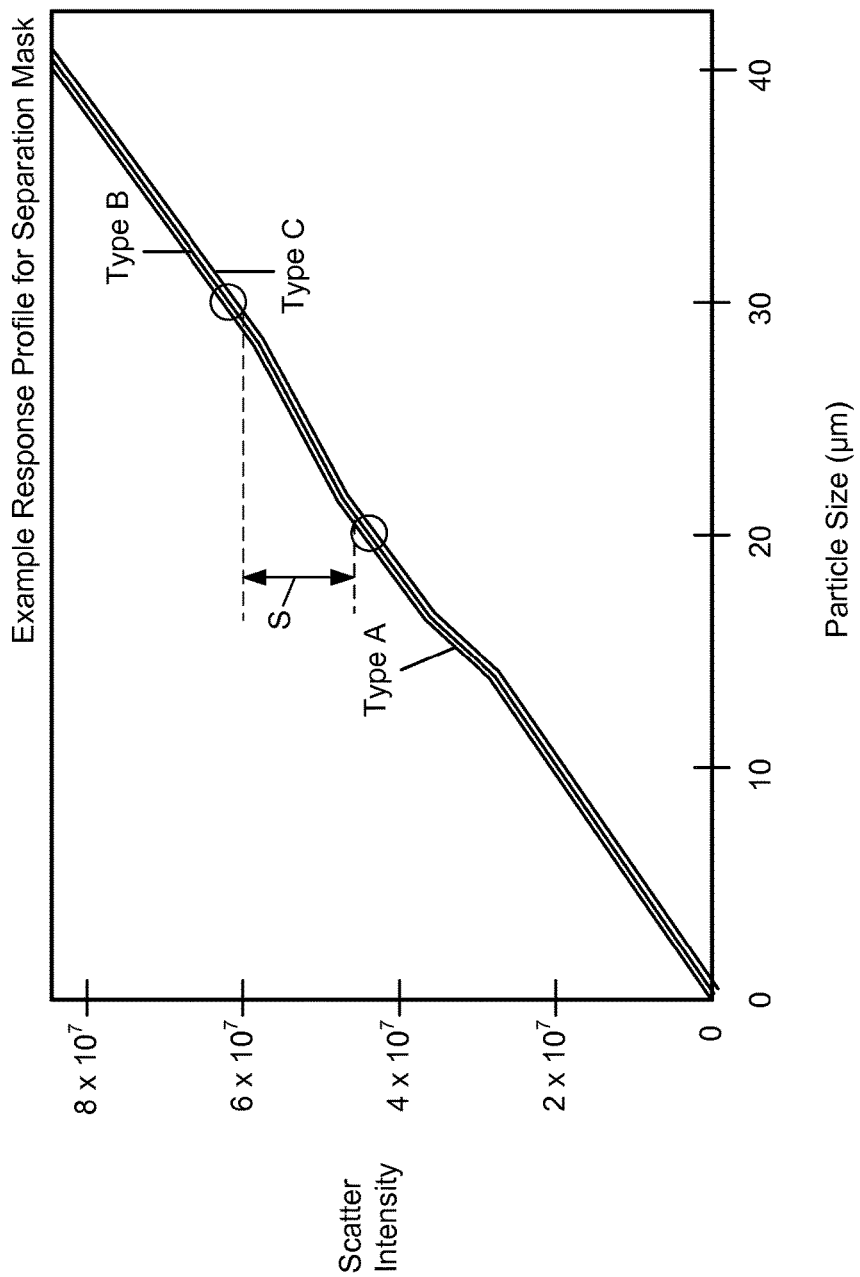
FIG. 13 is a schematic diagram illustrating an exemplary response profile for an example separation mask.

FIG. 13 is a schematic diagram illustrating an exemplary response profile for a separation mask. Some specific examples of separation masks are illustrated and described with reference to FIGS. 8-9. Response profiles for three different types of particles (Types A, B, and C) are illustrated. The specific data illustrated in FIG. 13 is hypothetical but provided to help illustrate the concepts discussed below.

A separation mask is a filter mask in which the radiation intensities detected for given particles sizes have as little variation as possible across multiple different types of particles. In a separation mask, reduced variation is more important than a linear response, and therefore the separation mask may have more ripple (i.e., greater path length) than a smoothness mask.

In the example shown in FIG. 13, the response profiles obtained with the separation mask are not perfectly linear. But, the response profiles for multiple different particle types (e.g., Types A, B, and C) are very close together. As a result, any of the particles (Types A, B, or C) having a size of 20

μm result in a detected radiation intensity of about $4.5 \times 10^7$, and particles having a size of 30 μm result in a detected radiation intensity of about $6 \times 10^7$. The separation mask is selected to maintain as much separation ("S" in FIG. 13) as possible in the radiation intensities detected for particles having different sizes, regardless of the type of the particle. For example, the separation S is difference in the radiation intensity detected for a particle of a given size (e.g., 20 μm) of type A, and the radiation intensity detected for a particle of a larger given size (e.g., 30 μm) of type C. If these radiation intensities overlap, then the separation of the filter mask is not adequate, because the cytometer may not be able to differentiate between the particles of different sizes. When they do not overlap, however, as shown in FIG. 13, the cytometer can distinguish between the two different sized particles, even though they are different types of particles. In fact, particles that are even closer in size could be distinguished from each other using the separation mask example shown in FIG. 12.

Because of the separation in the response profile provided by a separation mask, the separation mask can be used to determine differences in particle sizes even when particles of different types are present in the sample.

In some cases, even better results can be obtained by utilizing both a smoothness mask and a separation mask simultaneously in the cytometer to evaluate the particles within a sample. By separating the beam into two or more separate beams, such as shown in FIGS. 10-11, a smoothness mask can be inserted as one of the filter masks (e.g., $120^1$) and a separation mask can be inserted as another of the filter masks (e.g., $120^2$), to independently and simultaneously evaluate light rays associated with the same particle. For example, the radiation intensity determined using the separation mask can be used to determine the approximate size of the particle, regardless of the particle type. Using this information, the flow cytometer can then use the radiation intensity determined using the smoothness mask to determine the particle type and a more precise size of the particle. The results obtained by using two or more different filter masks simultaneously, can therefore generate better results than using either of the two or more filter masks by themselves.

Additional types of filters can also be used to obtain even more information regarding a sample. The filters can include one or more additional filter masks that selectively block or pass light rays based on radiation angle, or can include one or more spectral filters, neutral density filters, and polarizing filters.

Figure 14:
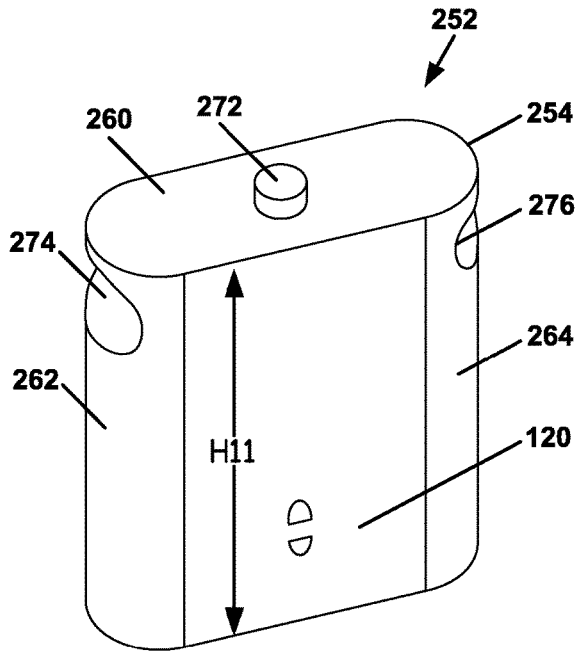
FIG. 14 is a front perspective view of an example mask holder.
Figure 16:
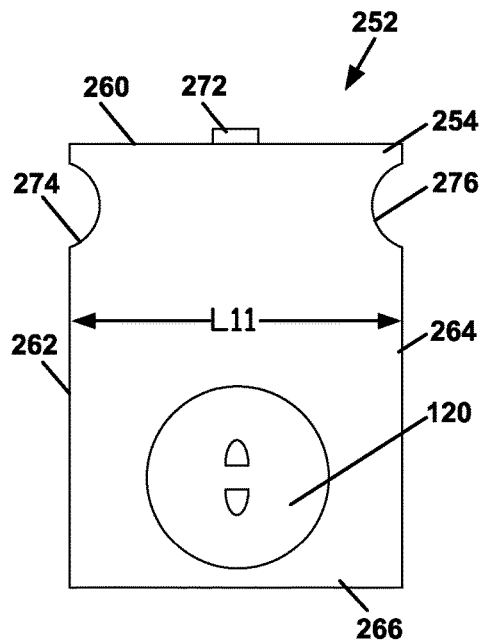
FIG. 16 is a front elevational view of the example mask holder shown in FIG. 14.
Figure 15:
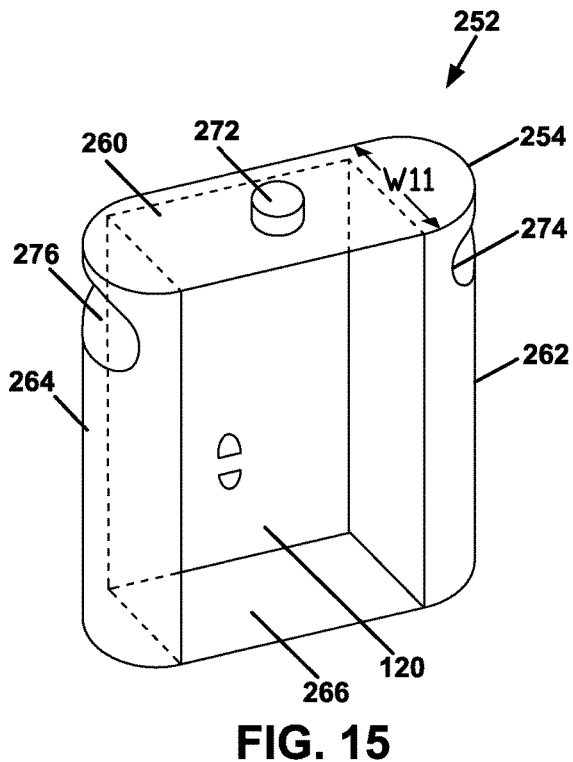
FIG. 15 is a rear perspective view of the example mask holder shown in FIG. 14.

FIGS. 14-16 illustrate an example mask holder 252, including a housing 254 and a filter mask 120. FIG. 14 is a front perspective view, FIG. 15 is a rear perspective view, and FIG. 16 is a front elevation view. In this example, the housing 254 includes a top 260, sides 262 and 264, and bottom 266. Also illustrated in this example are engagement feature 272, and grip features 274 and 276.

In this example, the housing 254 includes a top 260, sides 262 and 264, and bottom 266. In some embodiments, the flow cytometer 100 (FIG. 1) is configured to receive removable filter masks 120. In this example, the filter masks 120 are contained in mask holders 252 that can be easily inserted into or removed from the flow cytometer 100 as desired. A plurality of different mask holders 252 having different filter masks are provided in some embodiments, and the particular mask holder can be selected by the operator depending on the type of sample, or the type of evaluation to be performed, for example.

In some embodiments, the mask holder 252 is formed of a single piece of material. The mask holder 252 can be molded for example. In another possible embodiment, the mask holder 252 is formed of a solid piece of material which is then machined, etched, or otherwise formed into the desired configuration. In other embodiments, the mask holder 252 is formed of two or more pieces of material. Examples of possible materials include plastic, metal, glass, and combinations of these or other materials. One or more coatings can also be applied, such as a paint. In some embodiments the materials and/or coatings are light absorbent and/or non-reflective.

The housing 254 is sized and shaped, in some embodiments, for insertion within a correspondingly sized receptacle aligned at the appropriate location within the optics system of the cytometer.

In some embodiments, the top 260 includes an engagement feature 272. A cover or latch over the cytometer's receptacle is configured to engage with the engagement feature 272 when the mask holder 252 is properly inserted into the receptacle.

In some embodiments, sides 262 and 264 include grip features 274 and 276. In this example, the grip features 274 and 276 are configured to be grasped by tips of the operator's fingers to permit easier removal of the mask holder 252 from the cytometer's receptacle.

In some embodiments, the mask holder 252 has a height H11, a length L11, and a width W11 as shown in FIGS. 14-16. Various embodiments can have various sizes. As one example, the height H11 and the length L11 are in a range from about 0.5 inches to about 2 inches. Some embodiments have a height H11 and a length L11 of about 1 inch. As another example, the width W11 is in a range from about 0.1 inches to about 0.5 inches. Some embodiments have a width W11 of about 0.25 inches.

In some embodiments a thickness of the filter mask 120 is less than the width W11 of the mask holder 252. As one example, the thickness is in a range from about 10 thou to about 30 thou. Some embodiments have a thickness of about 20 thou (0.5 mm).

The mask holder 252 illustrated herein is provided by way of example, but a wide variety of alternative configurations are also possible.

As described herein, some embodiments of the flow cytometer 100 include one or more types of computer readable media. Computer readable media includes any available media that can be accessed by the computing device 112. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 112. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

In some embodiments, the term "substantially" refers to a deviation of less than 5%. In other embodiments, the term refers to a deviation of less than 1%. Yet other embodiments have a deviation of less than 0.1%. Other embodiments have other magnitudes of deviation.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A filter mask for use in a flow cytometer, the filter mask comprising:
    a body including:
        light blocking features including:
            an outer blocker extending between an outer edge and an inner edge, the inner edge being positioned around an origin point;
            a central blocker extending through the origin point and between opposite sides of the inner edge of the outer blocker;
            a bullseye blocker centered around the origin point and overlapping the central blocker; and
            a secondary blocker extending between the opposite sides of the inner edge of the outer blocker at a distance away from the origin point, the secondary blocker configured to block a portion of light rays having radiation angles between maximum and minimum radiation angles; and
        light passing apertures defined by spaces between the inner edge of the outer blocker, the central blocker, and the secondary blocker, and configured to permit light rays to pass through the body.

2. The filter mask of claim 1, wherein the outer blocker is arranged and configured to block light rays within the flow cytometer associated with radiation angles greater than maximum vertical and horizontal radiation angles.

3. The filter mask of claim 1, wherein the secondary blocker is arranged and configured to block at least some light rays within the flow cytometer associated with radiation angles less than the maximum vertical and horizontal radiation angles, and is positioned between the outer blocker and an origin point of the filter mask.

4. The filter mask of claim 3, wherein the secondary blocker has a rectangular shape.

5. The filter mask of claim 3, wherein the secondary blocker has a curved shape.

6. The filter mask of claim 1, wherein the filter mask is contained in a mask holder.

7. The filter mask of claim 1, wherein the filter mask is a smoothness filter having a substantially linear response profile for a single type of particle.

8. The filter mask of claim 1, wherein the filter mask is a separation filter having a separation in the response profiles of particles of different types.

9. A flow cytometer comprising:
    a flow nozzle configured to provide a fluid along a flow path, the fluid including sample particles therein;
    a light source configured to generate a light beam directed toward the flow path, wherein when the light beam intersects with the flow path, light rays are radiated by the fluid and the particles at radiation angles;
    an optics system configured to receive the radiated light rays and to direct the light rays along an optical path, the optics assembly including at least a first filter mask, wherein the first filter mask is the filter mask of claim 1; and
    a sensor analyzer arranged at an end of the optical path to collect and analyze light rays passing through the optics system.

10. The flow cytometer of claim 9, wherein the optics system comprises a receptacle, and wherein the first filter mask is removable from the receptacle.

11. The flow cytometer of claim 9, wherein the optics system further comprises:
    a beam separating assembly arranged along the optical path to separate the light rays into at least two separate beams, wherein the first filter mask is arranged along a first of the separate beams; and
    a second filter mask arranged along a second of the separate beams.

12. The flow cytometer of claim 11, wherein the first filter mask passes light rays having a first set of radiation angles, and wherein the second filter mask passes light rays having a second set of radiation angles.

13. The flow cytometer of claim 12, wherein at least some of the radiation angles are the same in the first set and the second set.

14. A method of evaluating a particle with a flow cytometer, the method comprising:
    passing a particle in a fluid along a fluid flow path;
    illuminating the particle and the fluid with a light beam;
    collecting light rays radiated from the fluid and the light beam with an optics system;
    selectively blocking some of the light rays having certain radiation angles with a first filter mask, wherein the first filter mask is the filter mask of claim 1;
    selectively passing some of the light rays with the first filter mask; and
    detecting light rays passed by the first filter mask with a sensor analyzer to evaluate at least one characteristic of the particle.

15. The method of claim 14, wherein the at least one characteristic is selected from a size of the particle and a type of the particle.

16. The method of claim 14, further comprising separating the light beam into at least two separate beams with the optics system.

17. The method of claim 16, wherein the selectively blocking and the selectively passing involves a first set of separate beams using the first the filter mask, and further comprising: selectively blocking some of the light rays of a second set of separate beams having certain radiation angles using a second filter mask, wherein the radiation angles blocked with the second filter mask are different than the radiation angles blocked with the first filter mask.

18. The method of claim 14, further comprising:
    receiving the first filter mask into a receptacle of the flow cytometer, the first filter mask being housed in a mask holder, wherein receiving the first filter mask into a receptacle of the flow cytometer occurs before passing the particle in the fluid along the fluid flow path.

19. The filter mask of claim 1, wherein the secondary blocker extends in a horizontal direction at a distance above the origin point.

20. The filter mask of claim 1, wherein the secondary blocker extends in a horizontal direction at a distance below the origin point.

21. The filter mask of claim 1, wherein the secondary blocker comprises first and second portions, each portion positioned at an opposite side of the origin point.

22. The filter mask of claim 1, wherein the central blocker is configured for blocking light rays having radiation angles less than a minimum vertical radiation angle.

23. The filter mask of claim 1, wherein the bullseye blocker is configured to block light rays that are not radiated and that have a radiation angle less than the minimum radiation angle.

24. The filter mask of claim 1, wherein the central blocker has a rectangular shape and the bullseye blocker has a rounded shape.

25. The filter mask of claim 1, wherein the central blocker has a first outer edge defining a first half distance from the origin point,
   wherein the bullseye blocker has a second outer edge defining a second half distance from the origin point, and
   wherein the second half distance is larger than the first half distance.

* * * * *

UNITED STATES PATENT AND TRADEMARK OFFICE
CERTIFICATE OF CORRECTION

PATENT NO. : 9,885,603 B2
APPLICATION NO. : 14/776878
DATED : February 6, 2018
INVENTOR(S) : Morrell et al.

Page 1 of 1

It is certified that error appears in the above-identified patent and that said Letters Patent is hereby corrected as shown below:

In the Claims

Column 16, Line 59, Claim 17: "the first the filter mask, and further" should read --the first filter mask, and further--

Signed and Sealed this
Twenty-ninth Day of October, 2019

Andrei Iancu
*Director of the United States Patent and Trademark Office*